(12) United States Patent
Diaz et al.

(10) Patent No.: US 7,927,650 B2
(45) Date of Patent: Apr. 19, 2011

(54) SYSTEM AND METHOD FOR LOADING A BENEFICIAL AGENT INTO A MEDICAL DEVICE

(75) Inventors: Stephen Hunter Diaz, Palo Alto, CA (US); Theodore L. Parker, Danville, CA (US)

(73) Assignee: Innovational Holdings, LLC, New Brunswick, NJ (US)

( * ) Notice: Subject to any disclaimer, the term of this patent is extended or adjusted under 35 U.S.C. 154(b) by 1239 days.

(21) Appl. No.: 11/392,184

(22) Filed: Mar. 28, 2006

(65) Prior Publication Data

US 2006/0177564 A1 Aug. 10, 2006

Related U.S. Application Data

(63) Continuation-in-part of application No. 09/948,989, filed on Sep. 7, 2001, now Pat. No. 7,208,010.

(60) Provisional application No. 60/314,259, filed on Aug. 20, 2001, provisional application No. 60/667,564, filed on Mar. 31, 2005.

(51) Int. Cl.
  *B05D 3/10* (2006.01)
  *B05D 1/12* (2006.01)

(52) U.S. Cl. ....... 427/2.1; 427/2.24; 427/2.25; 427/180; 427/189; 427/331; 427/335

(58) Field of Classification Search .................. 427/2.1, 427/2.24, 2.25, 180, 189, 331, 335, 227
See application file for complete search history.

(56) References Cited

U.S. PATENT DOCUMENTS

| | | | |
|---|---|---|---|
| 4,733,665 A | 3/1988 | Palmaz | |
| 4,739,762 A | 4/1988 | Palmaz | |
| 4,776,337 A | 10/1988 | Palmaz | |
| 4,969,458 A | 11/1990 | Wiktor | |
| 6,241,762 B1 | 6/2001 | Shanley | |
| 6,558,733 B1 * | 5/2003 | Hossainy et al. | 427/2.24 |
| 6,913,617 B1 * | 7/2005 | Reiss | 623/1.15 |
| 6,916,379 B2 * | 7/2005 | Shekalim et al. | 118/669 |
| 2003/0082680 A1 | 5/2003 | Hostetter et al. | |
| 2004/0073294 A1 | 4/2004 | Diaz et al. | |
| 2004/0234748 A1 * | 11/2004 | Stenzel | 428/327 |
| 2004/0238978 A1 | 12/2004 | Diaz | |
| 2005/0055078 A1 | 3/2005 | Campbell | |
| 2005/0209681 A1 * | 9/2005 | Curcio et al. | 623/1.15 |

FOREIGN PATENT DOCUMENTS

| | | |
|---|---|---|
| DE | 10200387 B4 | 11/2009 |
| WO | WO 02/26162 A2 | 4/2002 |
| WO | WO 0226162 A2 * | 4/2002 |

OTHER PUBLICATIONS

European Search Report dated Jun. 1, 2010 for European Application No. 06739863.6.
Australian Office Action dated Aug. 10, 2010 for Australian Application No. 2006230204.

* cited by examiner

*Primary Examiner* — Timothy H Meeks
*Assistant Examiner* — Cachet I Sellman

(57) ABSTRACT

The beneficial agent is applied into the holes in a medical device in a dry particulate form and is adhered in the hole in a manner that allows release of the drug in a controlled manner. The drug material would be formed into particles and placed in the holes. The solvent would be added to partially liquefy and adhere the drug into the holes. After application of the solvent, the particles are adhered together in a substantially uniform drug containing matrix. The particles may include drug alone or drug in combination with other materials including a matrix.

22 Claims, 2 Drawing Sheets

SYSTEM AND METHOD FOR LOADING A BENEFICIAL AGENT INTO A MEDICAL DEVICE

CROSS REFERENCE TO RELATED APPLICATIONS

This application claims priority to U.S. Provisional Patent Application Ser. No. 60/667,564, filed Mar. 31, 2005. This application also claims priority to U.S. patent application Ser. No. 09/948,989, filed Sep. 7, 2001, which claims priority to U.S. Provisional Patent Application Ser. No. 60/314,25, filed Aug. 20, 2001. The entire contents of both are incorporated herein by reference.

FIELD OF THE INVENTION

The invention relates to a method and apparatus for loading a beneficial agent, such as a drug into a medical device, such as a stent.

DESCRIPTION OF THE RELATED ART

Implantable medical devices are often used for delivery of a beneficial agent, such as a drug, to an organ or tissue in the body at a controlled delivery rate over an extended period of time. These devices may deliver agents to a wide variety of bodily systems to provide a wide variety of treatments.

One of the many implantable medical devices which have been used for local delivery of beneficial agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as stainless steel, gold, silver, tantalum, titanium, and shape memory alloys, such as Nitinol, and biodegradable materials including biodegradable polymers and biodegradable metal alloys.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. Despite the introduction of improved surgical techniques, devices, and pharmaceutical agents, the overall restenosis rates for bare metal stents are still reported in the range of 10% to 25% within six to twelve months after an angioplasty procedure. To treat this condition, additional revascularization procedures are frequently required, thereby increasing trauma and risk to the patient.

One of the techniques recently introduced to address the problem of restenosis is the use of surface coatings of various drugs on stents. Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall and increased risk of cracking, flaking, or separating from the stent.

In addition, it is not currently possible to deliver many drugs with a surface coating due to sensitivity of the drugs to water, other compounds, or conditions in the body which degrade the drugs. Lack of drug capacity and lack of control over delivery also limit the usefulness of surface coatings for many drugs.

U.S. Patent Publication 2004/0073294 describes systems and methods for loading a beneficial agent into holes in a medical device, such as a stent. This process uses a computer guided micro dispenser to load droplets of liquid solution into the holes of the stent. The stents are mounted on a rubber coated mandrel blocking the bottoms of the holes. A machine, using machine vision, maps the exact locations of each of the target holes and then moves each hole under the dispenser that then shoots liquid into the holes. The filled stent is dried in an oven, and then a next deposit is applied. Subsequent deposits of polymer and polymer/drug are applied to achieve the desired release properties.

This process has some advantages. It is a non-contact process, so there is little drag of material from hole to hole and no back contamination. It is very fast, filling at least 10 holes per second. The dispenser can be turned on and off very quickly, so complex patterns of filling can be supported. It has proven results of accuracy and consistency.

The liquid droplet method also has some limitations. The piezoelectric dispenser generally requires solutions with low viscosities. Therefore, the solids content should remain low, often less than 5%. The low solids content can result in the need for many deposits to build up a sufficient amount of beneficial agent. In addition, the solid should be very soluble in the solvent. This may require the use of solvents that have undesirable properties. Finally, the oven drying step is too hot for some drugs or proteins.

Accordingly, it would be desirable to provide a system and method for loading a beneficial agent into an expandable medical device, such as a stent, which can deliver compositions with higher solids content and/or can operate with limited drying time or low drying temperature.

SUMMARY OF THE INVENTION

The present invention relates to a system and method for loading a beneficial agent in a medical device wherein the beneficial agent is in the form of particles.

In accordance with one aspect of the invention, a method for loading a medical device with a beneficial agent comprises the steps of providing a medical device with a plurality of holes, delivering a plurality of particles of drug into the plurality of holes in a dry form, and delivering a liquefying substance into the plurality of holes. The liquefying substance liquefies at least a portion of the particles and adheres the drug in the holes.

In accordance with another aspect of the invention, a method for loading a medical device with a beneficial agent comprises the steps of providing a medical device with a plurality of holes, forming a plurality of particles comprising a beneficial agent, delivering the plurality of particles into the plurality of holes, and securing the particles in the holes. The particles are sized to fit as a plug with a single particle in each of the plurality of holes.

In accordance with a further aspect of the invention, a system for loading a medical device with a beneficial agent is comprised of a particle delivery system for delivery of particles of drug into a plurality of holes in a medical device and a solvent delivery system for delivery of a liquid solvent into the plurality of holes in the medical device.

BRIEF DESCRIPTION OF THE DRAWINGS

The invention will now be described in greater detail with reference to the preferred embodiments illustrated in the accompanying drawings, in which like elements bear like reference numerals.

DETAILED DESCRIPTION OF THE INVENTION

Figure 1A:
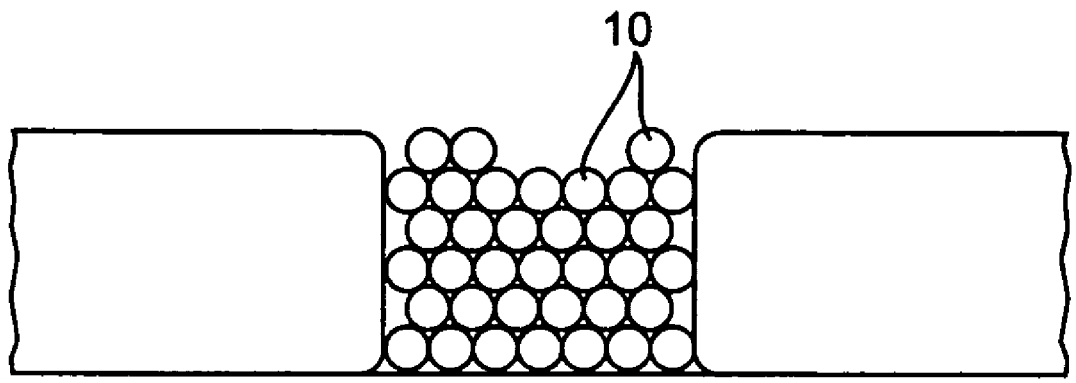
FIGS. 1A-1C are side cross sectional views of a hole in a medical device being loaded by a first method of the present invention.

The present invention relates to a method and apparatus for loading a beneficial agent into a medical device. More particularly, the invention relates to a method and apparatus for loading a beneficial agent in a stent.

First, the following terms, as used herein, shall have the following meanings:

The term "beneficial agent" as used herein is intended to have its broadest possible interpretation and is used to include any therapeutic agent or drug, as well as inactive agents such as barrier layers, carrier layers, therapeutic layers or protective layers.

The terms "drug" and "therapeutic agent" are used interchangeably to refer to any therapeutically active substance that is delivered to a living being to produce a desired, usually beneficial, effect. The present invention is particularly well suited for the delivery of antineoplastic, angiogenic factors, immuno-suppressants, anti-inflammatories and antiproliferatives (anti-restenosis agents) such as paclitaxel and Rapamycin for example, and antithrombins such as heparin, for example.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, a therapeutic agent, an activating agent or a deactivating agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "bioresorbable" refers to a matrix, as defined herein, that can be broken down by either chemical or physical process, upon interaction with a physiological environment. The bioresorbable matrix is broken into components that are metabolizable or excretable, over a period of time from minutes to years, preferably less than one year, while maintaining any requisite structural integrity in that same time period.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000.

The term "holes" refers to holes of any shape and includes both through-holes and recesses.

Implantable Medical Devices with Holes

U.S. Pat. No. 6,241,762 illustrates a medical device in the form of a stent designed with large, non-deforming struts, which can contain holes without compromising the mechanical properties of the struts, or the device as a whole. The non-deforming struts can be achieved by the use of ductile hinges which are described in detail in U.S. Pat. No. 6,241,762, which is incorporated hereby by reference in its entirety. The holes serve as large, protected reservoirs for delivering various beneficial agents to the device implantation site.

The holes can be circular, oval, rectangular, polygonal, D-shaped, or other shaped and can extend through the thickness of the medical device. The volume of beneficial agent that can be delivered using holes is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs to achieve clinical efficacy without the undesirable side-effects of more potent drugs.

According to one example, the total depth of the holes is about 100 to about 140 microns (about 0.0039 to about 0.0055 inches), typically 125 microns (0.0049 inches) for stainless steel. For stronger alloys, such as commercially available cobalt chromium alloys, the stent may be somewhat thinner. For example, the total depth of the holes is about 60 to about 100 microns (about 0.0026 to about 0.0039 inches) for cobalt chromium alloys. According to one preferred embodiment of the present invention, each of the holes have an area of at least $5 \times 10^{-6}$ square inches, and preferably at least $10 \times 10^{-6}$ square inches. A square hole having a width of about 0.005 inches will have an hole area of about $25 \times 10^{-6}$ square inches.

Uses for Implantable Medical Devices

Although the present invention has been described with reference to a medical device in the form of a stent, the medical devices of the present invention can also be medical devices of other shapes useful for site-specific and time-release delivery of drugs to the body including the heart and other organs and tissues. The drugs may be delivered to the vasculature including the coronary and peripheral vessels for a variety of therapies, and to other lumens in the body. The drugs may increase lumen diameter, create occlusions, or deliver the drug for other reasons. The medical devices can take a variety of shapes including cylinders, spheres, coils, filament, mesh, and other shapes.

Medical devices and stents, as described herein, are useful for the prevention of amelioration of restenosis, particularly after percutaneous transluminal coronary angioplasty and intraluminal stent placement. In addition to the timed or sustained release of anti-restenosis agents, other agents such as anti-inflammatory agents may be incorporated into the microstructures incorporated in the plurality of holes within the device. This allows for site-specific treatment or prevention any complications routinely associated with stent placements that are known to occur at very specific times after the placement occurs.

Systems and Methods for Loading a Beneficial Agent into a Medical Device

The beneficial agent is applied into the holes in a medical device in a dry particulate form and is adhered in the hole in a manner that allows release of the drug in a controlled manner.

According to a first embodiment, a machine very similar to the dropwise filling machine described in U.S. Patent Publication 2004/0073294, which is incorporated herein by reference in its entirety, is used to deliver a slow drying solvent into the holes in a dropwise manner. Alternatively, the slow drying solvent can be delivered into the holes in other manners. The hole should only be partially filled with solvent, for example, the solvent can fill about 10% to about 80% of the hole.

Figure 1B:
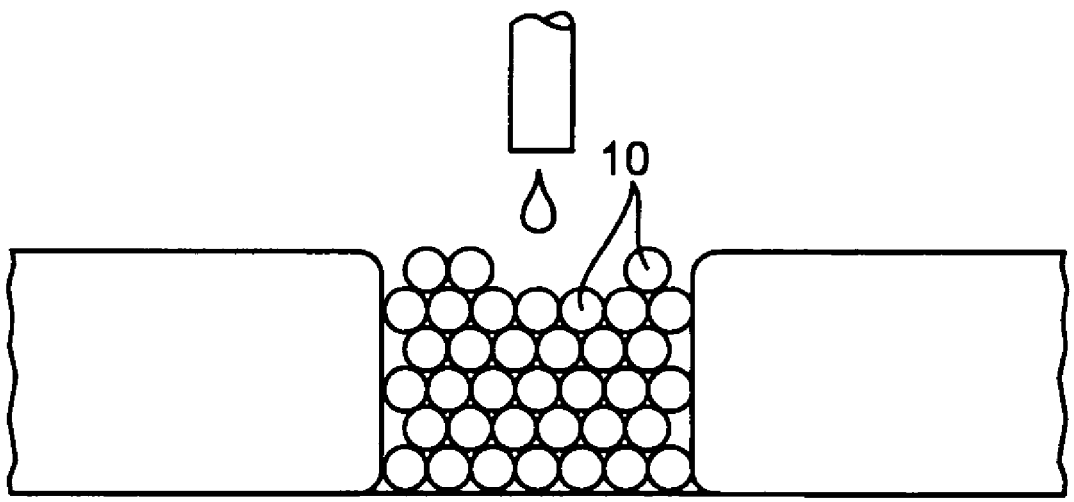
Figure 1C:
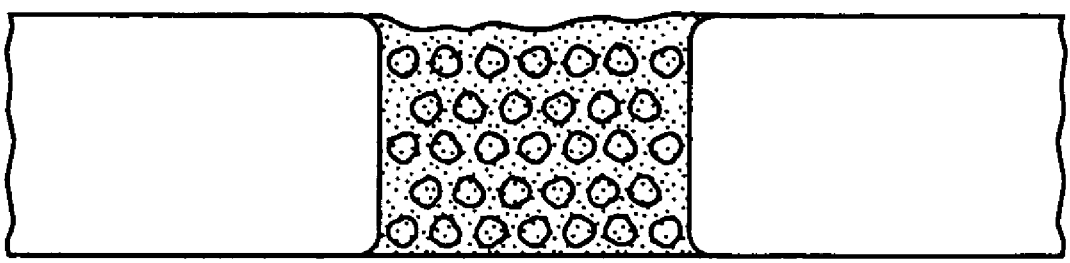

The drug material would be formed into particles 10 and placed in the holes as shown in FIG. 1A. The solvent would be added as shown in FIG. 1B to partially liquefy and adhere the drug into the holes. After application of the solvent, the particles are adhered together in a substantially uniform drug containing matrix, as shown in FIG. 1C. The particles may include drug alone or drug in combination with other materials including a matrix.

Figure 2A:
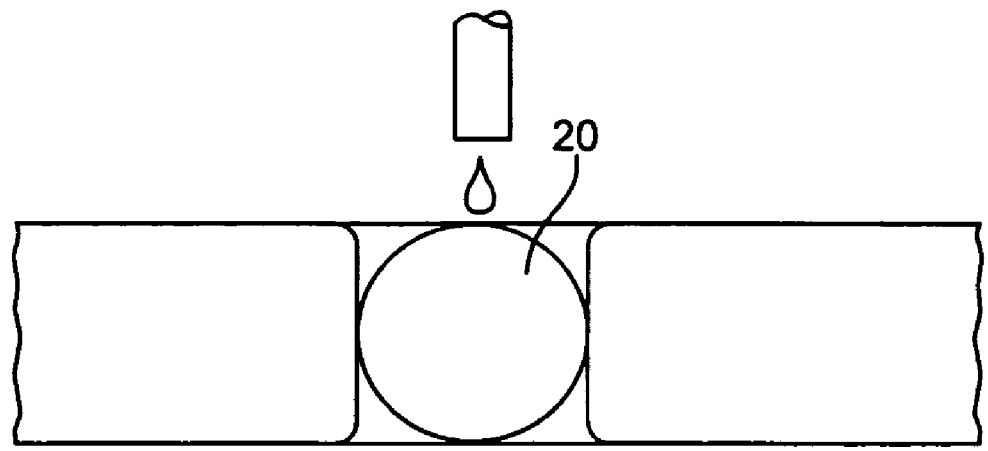
FIGS. 2A and 2B are side cross sectional views of a hole in a medical device being loaded by a second method of the present invention.
Figure 2B:
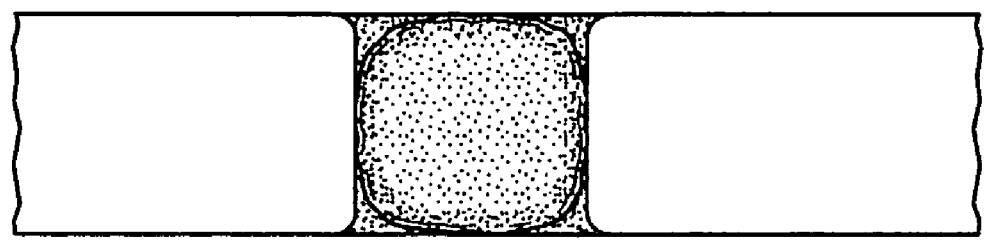

In one example shown in FIGS. 2A and 2B the particles are spheres 20 of about 0.005 inches in diameter, so that one sphere will fit in each hole. One example of the formation of spheres which fit with a single sphere in each hole is shown in U.S. Publication No. 2003/0082680 which is incorporated herein by reference in its entirety. Upon application of the solvent the sphere is adhered within the hole as shown in FIG. 2B.

Figure 3:
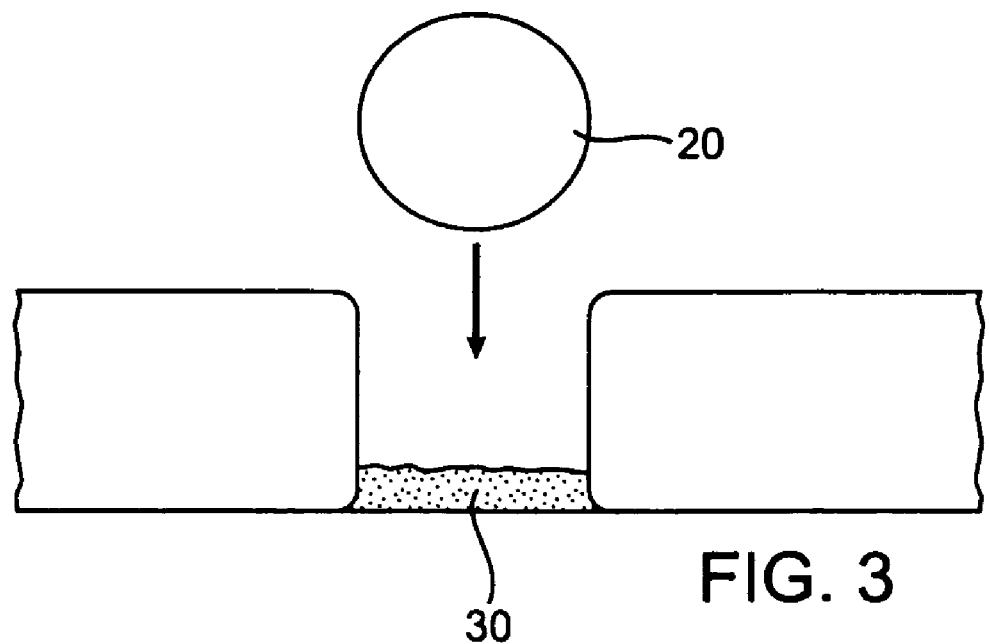
FIG. 3 is a side cross sectional view of a hole in a medical device being loaded by a third method of the present invention.

Alternately, the spheres or particles can be sized smaller so that a plurality of spheres or particles fit in each hole. The particles can be dropped, shot, or sprayed out of a tube that is positioned over the hole. This can be performed with a computer controlled jetting device, such as a piezoelectric microjet. In another embodiment of FIG. 3 the solvent 30 is first applied t6o the hole, such as with a dropwise filler. The sphere 20 then drops into the solvent and sticks in the hole. The solvent then causes the sphere to soften, expand, and become bonded or adhered to the walls of the hole.

The release kinetics of the microstructure created within the holes can be modified by using multi-layer spheres with the layers having different compositions to control the release. For example, a sphere with a central drug/polymer core can be surrounded by a polymer only layer with can form a barrier layer to control delivery of the drug.

As an alternative to depositing the particles in the holes by a controlled jetting process, the holes can be loaded with particles by dipping. For example, a mandrel having one or more stents with solvent filled holes can be immersed in an ocean of particles or spheres, such as in a fluidized bed. The particles that contacted the solvent at the bottom of the holes will stick there, and the others will fall off.

Yet another method of applying the particles is to use an electrostatic spraying method to apply the particles into the holes. The mandrel can be charged and the charged particles can be sprayed onto the stents. The sprayed spheres will stick all over the stents, but only the spheres falling into the holes will be bonded in place on the stent by the liquefying agent or solvent within the holes.

In an alternative embodiment, the process is reversed and the spheres are applied first. When the holes are slightly square or tapered (as they naturally are due to the laser cutting process), and if the spheres are just the right size, then they can be placed or wedged in the holes, but nowhere else on the stent. If the right combination of size distributions is achieved, and if the spheres are shot at the stent with some velocity, every hole will have a sphere stuck in it, perhaps with the aid of a static charge. After blowing or brushing off the excess spheres, the entire mandrel can be sprayed with solvent to soften the spheres lodged in the holes to force them to stick in place. Alternately, the solvent can be shot dropwise into the individual holes after filling them with spheres, as before.

Other particles including a simple powder or chopped fiber can be used as an alternative to the spheres. The concept with powder or other particles remains the same as with the spheres. Selective adhesion of the drug or drug/polymer matrix in the hole combined with a solvent or weak solution applied before or after application of the particles allows the drug or drug/polymer material to be permanently affixed in the holes.

In one embodiment, the particles and liquefying agents delivered into the holes can be loaded sequentially in layers with different compositions or concentrations in the layers. Different layers can be comprised of different therapeutic agents altogether, creating the ability to release different therapeutic agents at different points in time. The layers of beneficial agent provide the ability to tailor a drug delivery profile to different applications. This allows the medical device according to the present invention to be used for delivery of different beneficial agents to a wide variety of locations in the body.

A protective layer in the form of a cap layer can be provided at a tissue contacting surface of the stent. The cap layer can block or retard biodegradation of subsequent layers and/or block or retard diffusion of the beneficial agent in that direction for a period of time which allows the delivery of the medical device to a desired location in the body.

A barrier or base layer can also be used on the luminal (or mural) surface of the stent to achieve directional delivery of the therapeutic agent. The barrier or base layer can prevent the therapeutic agent from passing into the lumen and being carried away in the blood stream.

Other therapeutic agents for use with the present invention may, for example, take the form of small molecules, peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense oligonucleotides, monoclonal antibodies, platelets, prions, viruses, bacteria, eukaryotic cells such as endothelial cells, stem cells, ACE inhibitors, monocyte/macrophages and vascular smooth muscle cells. Such agents can be used alone or in various combinations with one another. For instance, anti-inflammatories may be used in combination with antiproliferatives to mitigate the reaction of tissue to the antiproliferative. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the matrix. Therapeutic agents may also be radioactive isotopes or agents activated by some other form of energy such as light or ultrasonic energy, or by other circulating molecules that can be systemically administered.

Exemplary classes of therapeutic agents include antiproliferatives, antithrombins (i.e., thrombolytics), immunosuppressants, antilipid agents, anti-inflammatory agents, antineoplastics including antimetabolites, antiplatelets, angiogenic agents, anti-angiogenic agents, vitamins, antimitotics, metalloproteinase inhibitors, NO donors, nitric oxide release stimulators, anti-sclerosing agents, vasoactive agents, endothelial growth factors, beta blockers, AZ blockers, hormones, statins, insulin growth factors, antioxidants, membrane stabilizing agents, calcium antagonists (i.e., calcium channel antagonists), retinoids, anti-macrophage substances, anti-lymphocytes, cyclooxygenase inhibitors, immunomodulatory agents, angiotensin converting enzyme (ACE) inhibitors, anti-leukocytes, high-density lipoproteins (HDL) and derivatives, cell sensitizers to insulin, prostaglandins and derivatives, anti-TNF compounds, hypertension drugs, protein kinases, antisense oligonucleotides, cardio protectants, petidose inhibitors (increase blycolitic metabolism), endothelin receptor agonists, interleukin-6 antagonists, anti-restenotics, vasodilators, and other miscellaneous compounds.

Antiproliferatives include, without limitation, paclitaxel, actinomycin D, rapamycin, everolimus, ZoMaxx, tacrolimus, cyclosporin, and pimecrolimus.

Antithrombins include, without limitation, heparin, aspirin, sulfinpyrazone, ticlopidine, ABCIXIMAB, eptifibatide, tirofiban HCL, coumarines, plasminogen, $\alpha_2$-antiplasmin, streptokinase, urokinase, bivalirudin, tissue plasminogen activator (t-PA), hirudins, hirulogs, argatroban, hydroxychloroquin, BL-3459, pyridinolcarbamate, Angiomax, and dipyridamole.

Immunosuppressants include, without limitation, cyclosporine, rapamycin and tacrolimus (FK-506), ZoMaxx, everolimus, etoposide, and mitoxantrone.

Antilipid agents include, without limitation, HMG CoA reductase inhibitors, nicotinic acid, probucol, and fibric acid derivatives (e.g., clofibrate, gemfibrozil, gemfibrozil, fenofibrate, ciprofibrate, and bezafibrate).

Anti-inflammatory agents include, without limitation, pimecrolimus, salicylic acid derivatives (e.g., aspirin, insulin, sodium salicylate, choline magnesium trisalicylate, salsalate, dflunisal, salicylsalicylic acid, sulfasalazine, and olsalazine), para-amino phenol derivatives (e.g., acetaminophen), indole and indene acetic acids (e.g., indomethacin, sulindac, and etodolac), heteroaryl acetic acids (e.g., tolmetin, diclofenac, and ketorolac), arylpropionic acids (e.g., ibuprofen, naproxen, flurbiprofen, ketoprofen, fenoprofen, and oxaprozin), anthranilic acids (e.g., mefenamic acid and meclofenamic acid), enolic acids (e.g., piroxicam, tenoxicam, phenylbutazone and oxyphenthatrazone), alkanones (e.g., nabumetone), glucocorticoids (e.g., dexamethaxone, prednisolone, and triamcinolone), pirfenidone, and tranilast.

Antineoplastics include, without limitation, nitrogen mustards (e.g., mechlorethamine, cyclophosphamide, ifosfamide, melphalan, and chlorambucil), methylnitrosoureas (e.g., streptozocin), 2-chloroethylnitrosoureas (e.g., carmustine, lomustine, semustine, and chlorozotocin), alkanesulfonic acids (e.g., busulfan), ethylenimines and methylmelamines (e.g., triethylenemelamine, thiotepa and altretamine), triazines (e.g., dacarbazine), folic acid analogs (e.g., methotrexate), pyrimidine analogs (5-fluorouracil, 5-fluorodeoxyuridine, 5-fluorodeoxyuridine monophosphate, cytosine arabinoside, 5-azacytidine, and 2',2'-difluorodeoxycytidine), purine analogs (e.g., mercaptopurine, thioguanine, azathioprine, adenosine, pentostatin, cladribine, and erythrohydroxynonyladenine), antimitotic drugs (e.g., vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin), phenoxodiol, etoposide, and platinum coordination complexes (e.g., cisplatin and carboplatin).

Antiplatelets include, without limitation, insulin, dipyridamole, tirofiban, eptifibatide, abciximab, and ticlopidine.

Angiogenic agents include, without limitation, phospholipids, ceramides, cerebrosides, neutral lipids, triglycerides, diglycerides, monoglycerides lecithin, sphingosides, angiotensin fragments, nicotine, pyruvate thiolesters, glycerolpyruvate esters, dihydoxyacetone-pyruvate esters and monobutyrin.

Anti-angiogenic agents include, without limitation, endostatin, angiostatin, fumagillin and ovalicin.

Vitamins include, without limitation, water-soluble vitamins (e.g., thiamin, nicotinic acid, pyridoxine, and ascorbic acid) and fat-soluble vitamins (e.g., retinal, retinoic acid, retinaldehyde, phytonadione, menaqinone, menadione, and alpha tocopherol).

Antimitotics include, without limitation, vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin.

Metalloproteinase inhibitors include, without limitation, TIMP-1, TIMP-2, TIMP-3, and SmaPI.

NO donors include, without limitation, L-arginine, amyl nitrite, glyceryl trinitrate, sodium nitroprusside, molsidomine, diazeniumdiolates, S-nitrosothiols, and mesoionic oxatriazole derivatives.

NO release stimulators include, without limitation, adenosine.

Anti-sclerosing agents include, without limitation, collagenases and halofuginone.

Vasoactive agents include, without limitation, nitric oxide, adenosine, nitroglycerine, sodium nitroprusside, hydralazine, phentolamine, methoxamine, metaraminol, ephedrine, trapadil, dipyridamole, vasoactive intestinal polypeptides (VIP), arginine, and vasopressin.

Endothelial growth factors include, without limitation, VEGF (Vascular Endothelial Growth Factor) including VEGF-121 and VEG-165, FGF (Fibroblast Growth Factor) including FGF-1 and FGF-2, HGF (Hepatocyte Growth Factor), and Ang1 (Angiopoietin 1).

Beta blockers include, without limitation, propranolol, nadolol, timolol, pindolol, labetalol, metoprolol, atenolol, esmolol, and acebutolol.

Hormones include, without limitation, progestin, insulin, the estrogens and estradiols (e.g., estradiol, estradiol valerate, estradiol cypionate, ethinyl estradiol, mestranol, quinestrol, estrond, estrone sulfate, and equilin).

Statins include, without limitation, mevastatin, lovastatin, simvastatin, pravastatin, atorvastatin, and fluvastatin.

Insulin growth factors include, without limitation, IGF-1 and IGF-2.

Antioxidants include, without limitation, vitamin A, carotenoids and vitamin E.

Membrane stabilizing agents include, without limitation, certain beta blockers such as propranolol, acebutolol, labetalol, oxprenolol, pindolol and alprenolol.

Calcium antagonists include, without limitation, amlodipine, bepridil, diltiazem, felodipine, isradipine, nicardipine, nifedipine, nimodipine and verapamil.

Retinoids include, without limitation, all-trans-retinol, all-trans-14-hydroxyretroretinol, all-trans-retinaldehyde, all-trans-retinoic acid, all-trans-3,4-didehydroretinoic acid, 9-cis-retinoic acid, 11-cis-retinal, 13-cis-retinal, and 13-cis-retinoic acid.

Anti-macrophage substances include, without limitation, NO donors.

Anti-leukocytes include, without limitation, 2-CdA, IL-1 inhibitors, anti-CD116/CD18 monoclonal antibodies, monoclonal antibodies to VCAM, monoclonal antibodies to ICAM, and zinc protoporphyrin.

Cyclooxygenase inhibitors include, without limitation, Cox-1 inhibitors and Cox-2 inhibitors (e.g., CELEBREX® and VIOXX®).

Immunomodulatory agents include, without limitation, immunosuppressants (see above) and immunostimulants (e.g., levamisole, isoprinosine, Interferon alpha, and Interleukin-2).

ACE inhibitors include, without limitation, benazepril, captopril, enalapril, fosinopril sodium, lisinopril, quinapril, ramipril, spirapril, and 2B3 ACE inhibitors.

Cell sensitizers to insulin include, without limitation, glitazones, P PAR agonists and metformin.

Antisense oligonucleotides include, without limitation, resten-NG.

Cardio protectants include, without limitation, VIP, pituitary adenylate cyclase-activating peptide (PACAP), apoA-I milano, amlodipine, nicorandil, cilostaxone, and thienopyridine.

Petidose inhibitors include, without limitation, omnipatrilat.

Anti-restenotics include, without limitation, include vincristine, vinblastine, actinomycin, epothilone, paclitaxel, paclitaxel derivatives (e.g., docetaxel), rapamycin, rapamycin derivatives, everolimus, tacrolimus, ZoMaxx, and pimecrolimus.

PPAR gamma agonists include, without limitation, farglitizar, rosiglitazone, muraglitazar, pioglitazone, troglitazone, and balaglitazone.

Miscellaneous compounds include, without limitation, Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic detergents may be used. Examples of nonionic additives include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEF and PEO) and polyvinyl pyrrolidone (PVP); carboxylic acids including D-lactic acid, glycolic acid, and propionic acid; detergents with affinity for hydrophobic interfaces including n-dodecyl-β-D-maltoside, n-octyl-β-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; CM-PEG; cholic acid; sodium dodecyl sulfate (SDS); docusate (AOT); and taumocholic acid.

While the invention has been described in detail with reference to the preferred embodiments thereof, it will be apparent to one skilled in the art that various changes and modifications can be made and equivalents employed, without departing from the present invention.

What is claimed is:

1. A method for loading a medical device with a beneficial agent, the method comprising:
   providing a medical device with a plurality of holes;
   delivering a plurality of particles of drug into the plurality of holes in a dry form; and
   delivering a liquefying substance into the plurality of holes, wherein the liquefying substance liquefies at least a portion of the particles and adheres the drug in the holes and is delivered into the plurality of holes before the particles are delivered to the holes.

2. The method of claim 1, wherein the plurality of particles of drug comprise spheres of drug.

3. The method of claim 2, wherein the spheres are sized to fit with a single sphere per hole.

4. The method of claim 2, wherein the spheres comprise a drug core and a polymer shell.

5. The method of claim 2, wherein the spheres comprise a mixture of drug and carrier.

6. The method of claim 2, wherein the spheres have a size of about 0.0001 to about 0.05 inches.

7. The method of claim 1, wherein the plurality of particles include a carrier.

8. The method of claim 7, wherein the carrier is a polymer.

9. The method of claim 8, wherein the plurality of particles of drug and polymer comprise a powder.

10. The method of claim 1, wherein the liquefying substance is a solvent.

11. The method of claim 1, wherein the particles are delivered into the holes in a plurality of layers.

12. The method of claim 1, wherein the particles are delivered into the holes by an electrostatic process.

13. The method of claim 1, wherein the liquefying substance is delivered into the plurality of holes in a dropwise manner.

14. The method of claim 12, wherein the liquefying substance is delivered into the plurality of holes by a computer controlled jetting process.

15. The method of claim 1, wherein the particles are delivered into the plurality of holes by immersion of the medical device into the particles.

16. A method for loading a medical device with a beneficial agent, the method comprising:
   providing a medical device with a plurality of holes;
   forming a plurality of particles comprising a beneficial agent, wherein the particles are sized to fit as a plug with a single particle in each of the plurality of holes;
   delivering the plurality of particles into the plurality of holes; and
   securing the particles in the holes.

17. The method of claim 16, wherein the particles are secured in the holes by backfilling with a liquid agent.

18. The method of claim 16, wherein the particles are secured in the holes by a liquid agent which liquefies at least a portion of the particles.

19. The method of claim 16, wherein the particles are spheres.

20. The method of claim 16, wherein the particles include a carrier.

21. The method of claim 20, wherein the carrier is a polymer.

22. The method of claim 16, wherein the particles are conical plugs.

* * * * *